(12) United States Patent
Kolberg et al.

(10) Patent No.: US 7,561,924 B2
(45) Date of Patent: Jul. 14, 2009

(54) ELECTRODE ARRANGEMENT

(75) Inventors: Gernot Kolberg, Berlin (DE); Hartmut Lenski, Glienick (DE); Max Schaldach, Erlangen (DE); Max Schaldach, Jr., legal representative, Berlin (DE); Curt Kranz, Berlin (DE)

(73) Assignee: Biotronik Mess -und Therapiegeraede GmbH & Co. Ingenieurbuero Berlin (DE)

( * ) Notice: Subject to any disclaimer, the term of this patent is extended or adjusted under 35 U.S.C. 154(b) by 1126 days.

(21) Appl. No.: 10/278,040

(22) Filed: Oct. 22, 2002

(65) Prior Publication Data
US 2003/0097051 A1 May 22, 2003

(30) Foreign Application Priority Data
Oct. 24, 2001 (DE) ................. 101 53 842

(51) Int. Cl.
*A61N 1/05* (2006.01)
(52) U.S. Cl. ..................................... 607/123
(58) Field of Classification Search ................ 600/309, 600/372–375, 381, 393; 607/115, 116, 119, 607/125–127, 122, 123; 606/129
See application file for complete search history.

(56) References Cited

U.S. PATENT DOCUMENTS

| | | | | |
|---|---|---|---|---|
| 4,402,329 A * | 9/1983 | Williams | ................ | 607/123 |
| 4,479,500 A | 10/1984 | Smits | | |
| 4,904,431 A * | 2/1990 | O—Maleki | ................ | 264/103 |
| 5,107,856 A * | 4/1992 | Kristiansen et al. | ......... | 607/126 |
| 5,267,958 A | 12/1993 | Buchbinder | | |
| 5,674,274 A * | 10/1997 | Morgan et al. | ............... | 607/123 |
| 5,738,683 A | 4/1998 | Osypka | | |
| 5,902,331 A * | 5/1999 | Bonner et al. | ............... | 607/122 |
| 5,954,761 A * | 9/1999 | Machek et al. | ............... | 607/126 |
| 5,957,967 A | 9/1999 | Laske | | |
| 5,964,796 A * | 10/1999 | Imran | ........................ | 607/122 |
| 6,056,722 A | 5/2000 | Jayaraman | | |
| 6,094,596 A | 7/2000 | Morgan | | |
| 6,095,990 A | 8/2000 | Parodi | | |
| 6,132,456 A | 10/2000 | Sommer | | |
| 6,185,464 B1 | 2/2001 | Bonner | | |
| 6,574,512 B1 * | 6/2003 | Zhang et al. | ................. | 607/122 |
| 2002/0007205 A1 | 1/2002 | Zheng | | |
| 2002/0026228 A1 * | 2/2002 | Schauerte | .................... | 607/122 |

FOREIGN PATENT DOCUMENTS

| | | |
|---|---|---|
| DE | 26 05 590 A1 | 8/1977 |
| DE | 44 25 195 C1 | 11/1995 |
| WO | WO 94/16619 A1 | 8/1994 |
| WO | WO 00/10639 A1 | 3/2000 |
| WO | WO 01/68177 A1 | 9/2001 |

\* cited by examiner

*Primary Examiner*—Angela D Sykes
*Assistant Examiner*—Michael Kahelin
(74) *Attorney, Agent, or Firm*—Hahn Loeser & Parks LLP (57) ABSTRACT

An intravascular electrode arrangement 10 includes a first and a second electrode line 12, 14 adapted for placement in blood vessels such as veins or arteries, each having at least one stimulation and/or sensing electrode in the region of the distal end of the respective electrode line, wherein there are longitudinal guides 18, 18', 18", 18''' provided externally on the first electrode line 12, 12', 12", 12''' for the second electrode line 14.

33 Claims, 5 Drawing Sheets

ELECTRODE ARRANGEMENT

The invention concerns an intravascular electrode arrangement including a first and a second electrode line adapted for placement in blood vessels such as veins or arteries, each having a stimulation and/or sensing electrode in the region of a distal end of the respective electrode line.

BACKGROUND OF THE ART

In the context of the present invention a distinction is drawn between intracardial electrode lines on the one hand and intravascular electrode lines on the other hand, in the sense that intracardial electrode lines are designed in such a way that their sensing or stimulation electrodes are placed after implantation in the atrium or ventricle of a heart while intravascular electrode lines, in the narrower sense used herein, are those electrode lines whose electrodes are disposed after the implantation operation in a blood vessel such as for example a vein or an artery. By virtue of the spatial restriction which prevails in such blood vessels the corresponding intravascular implantation locations are more difficult to aim for than intracardial implantation locations. In addition the intravascular implantation locations vary from one patient to another to a greater degree than is the case with intracardial implantation locations.

In connection with the stimulation of a heart, stimulation of the left part of the heart represents a problem for the reason that placement of intracardial electrodes in the left heart is highly complicated and expensive. Therefore, instead, to stimulate the left atrium or ventricle, use is made of intravascular electrodes which are introduced for example into coronary blood vessels. That gives rise to the problem referred to in the preceding paragraph.

SUMMARY OF THE INVENTION

In accordance with the invention that problem is resolved by an intravascular electrode arrangement of the kind set forth in the opening part of this specification, in which there are longitudinal guides disposed externally on the first electrode line for the second electrode line.

That solution is based on the notion of providing for the left atrium and the left ventricle of the heart, its own respective intravascular electrode catheter, which catheters are each of optimum configuration in regard to the different implantation locations. What is preferred in that connection is an electrode arrangement in which the first electrode line with the longitudinal guides is in the form of an atrial electrode catheter while the second electrode line serves to guide the first ventricular electrode line and is in the form of a ventricular electrode catheter. To implant those electrode lines, the ventricular electrode line is first introduced. That is easily possible in the usual manner as the ventricular electrode line does not have any guides. Then the atrial electrode line with its guides is pushed over the ventricular electrode line in such a way that the ventricular electrode line extends within the longitudinal guides. The atrial electrode line with its guides can then be advanced, being guided by the ventricular electrode line as it moves.

In order to permit as precise guidance as possible of the first electrode line, the longitudinal guides have eyes which are to be pushed over the second electrode line and which accordingly are adapted in respect of their inside diameter to the outside diameter of the second electrode line and substantially correspond thereto.

The diameter of the two electrode lines is preferably less than 2 mm so that they can be used as intravascular electrode lines.

In order to permit an electrode arrangement of the above-indicated kind, which include two electrode lines, first and foremost only one of the two electrode lines is to be modified in the manner in accordance with the invention in comparison with the state of the art while the second electrode line can correspond to the state of the art. Accordingly the way in which the above-indicated problem is solved in accordance with the invention already involves a single electrode line which is of a configuration in accordance with the invention, with longitudinal guides which are disposed externally on the electrode line and which preferably include eyes.

The longitudinal guides preferably include Nitinol, a nickel titanium alloy.

The longitudinal guides have in the longitudinal direction of the electrode line two ends of which preferably at least one of the ends has a slope which is inclined starting from the electrode line towards the respective other end. A particularly preferred variant is one in which both ends of the longitudinal guides are correspondingly beveled. Such a slope facilitates insertion of the electrode line or the electrode arrangement.

In a preferred configuration the slope of the longitudinal guides is formed by an open lattice structure or wire mesh. That lattice structure or the wire mesh is designed in particular in the manner of a stent.

Another preferred configuration is an electrode line in which the longitudinal guides are subsequently mounted to a casing or sheath of the electrode line. The alternative thereto involves longitudinal guides which are formed by the casing material itself so that longitudinal guides and the casing of the electrode line are formed together in one piece. In the preferred variant the casing of the electrode line and the longitudinal guides contain different materials, for example the casing of the electrode line is formed by silicone-bearing material while the longitudinal guides are formed substantially by Nitinol-bearing material, that is to say a metal.

In a preferred alternative configuration the longitudinal guides have friction-reducing tongues which are arranged between a hollow space of the longitudinal guides, which is provided to receive the second electrode line, and the casing of the first electrode line, and are of such a configuration that a casing of the second electrode line is at a spacing relative to the casing of the first electrode line by means of the tongues. Tongues affording that spacing can substantially avoid the casings of the two electrode lines directly rubbing against each other so that the two electrode lines can be displaced longitudinally as easily as possible relative to each other. In this connection the term tongue is used to denote any kind of spacing-affording constituent part of the longitudinal guides, in particular metal-bearing constituent parts of the longitudinal guide, which are arranged within the longitudinal guides between the two electrode lines.

In order finally to prevent a short-circuit or electrical contact of the sensing or stimulation electrodes of the one electrode line in relation to the electrodes of the second electrode line, it is provided that in particular the electrodes of the first electrode line are electrically insulated on that side of the periphery of the first electrode line, which by virtue of the longitudinal guides faces towards the second electrode line.

BRIEF DESCRIPTION OF THE DRAWINGS

The invention will now be described in greater detail by means of embodiments with reference to the accompanying drawings, in which identical parts are identified with identical reference numerals and wherein.

DETAILED DESCRIPTION OF A PREFERRED EMBODIMENT

Figure 1:
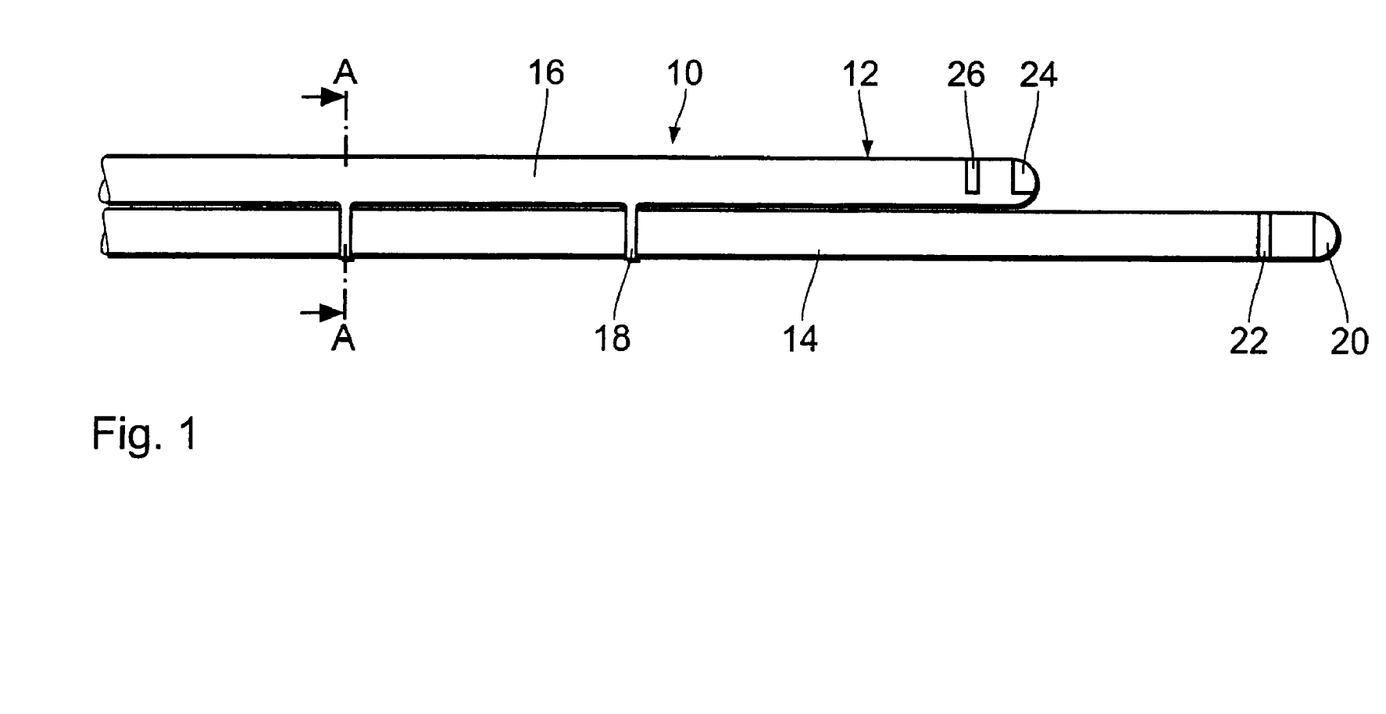
FIG. 1 shows a side view of an electrode arrangement with two electrode lines.

FIG. 1 shows an electrode arrangement 10 with an atrial electrode catheter 12 and a second ventricular electrode catheter 14. The two electrode catheters 12 and 14 are suitably designed by virtue of their diameter and flexibility for intravascular arrangement. In other words, the two intravascular electrode catheters 12 and 14 are thin and flexible enough to be placed in a blood vessel such as a vein or artery.

Both electrode catheters 12 and 14 have a sheath or casing of which the casing 16 of the atrial electrode catheter 12 is equipped with longitudinal guides 18 in the form of eyes which are adapted for longitudinally slidably accommodating the ventricular electrode catheter 14. A suitable material for the casings of the electrode catheters and for the longitudinal guides 18 is for example silicone which can be reinforced for example by stiffening comprising wire or the like in the region of the longitudinal guides 18.

Both electrode catheters 12 and 14 have stimulation and/or sensing electrodes at their respective distal end. The stimulation and sensing electrodes 20 and 22 of the ventricular electrode catheter 14 are in this respect designed in the usual manner in the form of a tip electrode 20 and a ring electrode 22. Suitable electrodes selectively permit unipolar or bipolar stimulation or sensing. Alternatively both electrode catheters may also be provided only with one electrode in the form of a tip or ring electrode.

The atrial electrode catheter 12 also has a tip electrode 24 and a ring electrode 26, wherein those two electrodes are electrically insulated on their side which faces towards the ventricular electrode line 14 so that no short-circuit occurs between the electrodes 20 and 22 of the ventricular electrode catheter 14 and the corresponding electrodes 24 and 26 of the atrial electrode catheter 12 if the distal ends of the two electrode catheters are at the same level upon longitudinal displacement of the atrial electrode catheter with respect to the ventricular electrode catheter 12.

Figure 7:
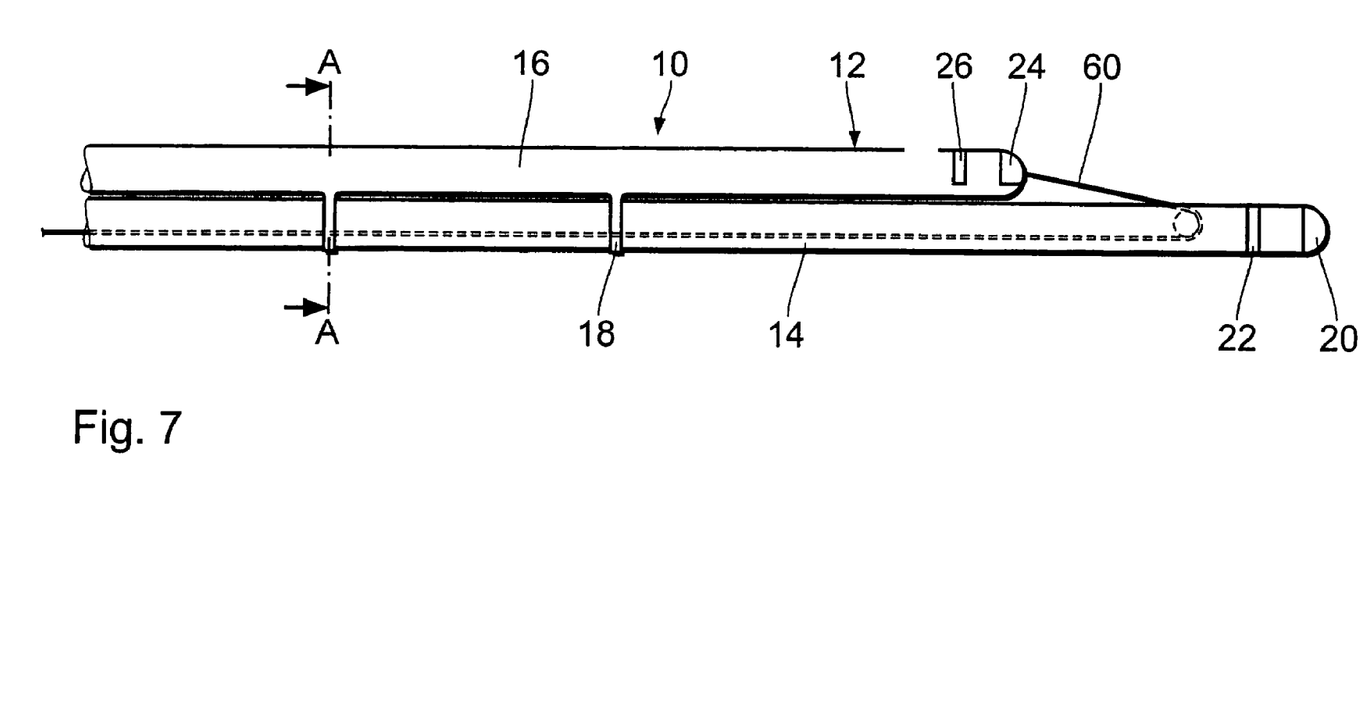
FIG. 7 shows an alternative embodiment similar to FIG. 1.

In the case of the implantation procedure firstly the ventricular electrode line is introduced into the blood vessels of a patient in such a way that the distal end of the electrode line 14 assumes with its electrodes 20 and 22 the desired target location, for example in the coronary sinus. Then the eyes 18 of the atrial electrode line 12 are pushed onto the ventricular electrode line 14 at the proximal end of the electrode line 14 so that the atrial electrode line is guided by means of its eyes 18 by the ventricular electrode line 14 which is already implanted. When the distal end of the atrial electrode line 12 has also reached the intended target location in the atrium of the heart the atrial electrode line 12 is fixed by clamping by means of its eyes 18 with respect to the ventricular electrode line 14. Suitable eyes 18 which permit such a clamping effect are shown in FIG. 7.

Figure 2:
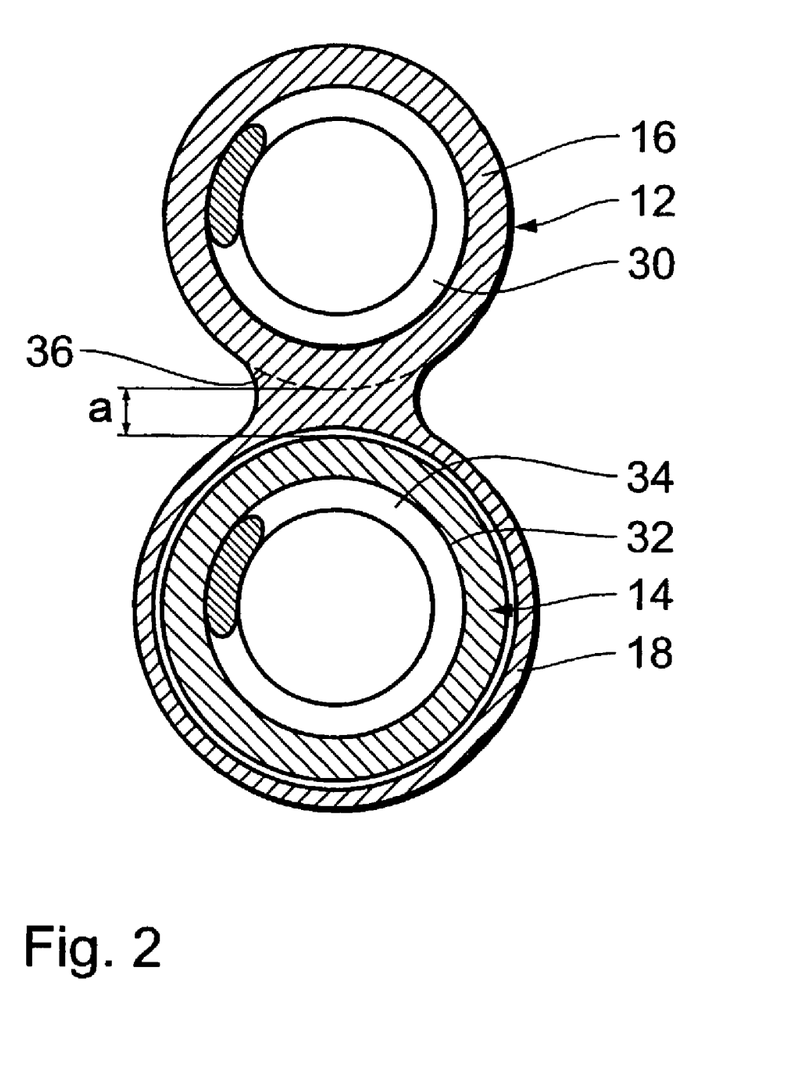
FIG. 2 is a view on an enlarged scale of the section shown at A-A in FIG. 1.

FIG. 2 shows a view in section through the electrode arrangement of FIG. 1 in the region of one of the longitudinal guides 18. As can be seen from FIG. 2 the longitudinal guide 18 is a constituent part of the casing 16 of the atrial electrode line 12. Arranged within the casing 16 of the atrial electrode line 12 is a stiffening helical coil 30 of metal.

The ventricular electrode line 14 is of a similar structure to the atrial electrode line 12, except that it does not have any longitudinal guides 18. The ventricular electrode line 14 also has a casing 32 for example of silicone and a stiffening metal coil 34 arranged therein. The outside diameter of the casing 32 is somewhat less than the inside diameter of the longitudinal guide 18 in order to permit mobility of the atrial electrode line 12 with respect to the ventricular electrode line 14.

The longitudinal guide 18 is so designed that the casings 16 and 32 of the atrial and ventricular electrode lines 12 and 14 respectively are at a spacing a from each other, as is indicated by the broken line 36 in FIG. 2.

Figure 3:
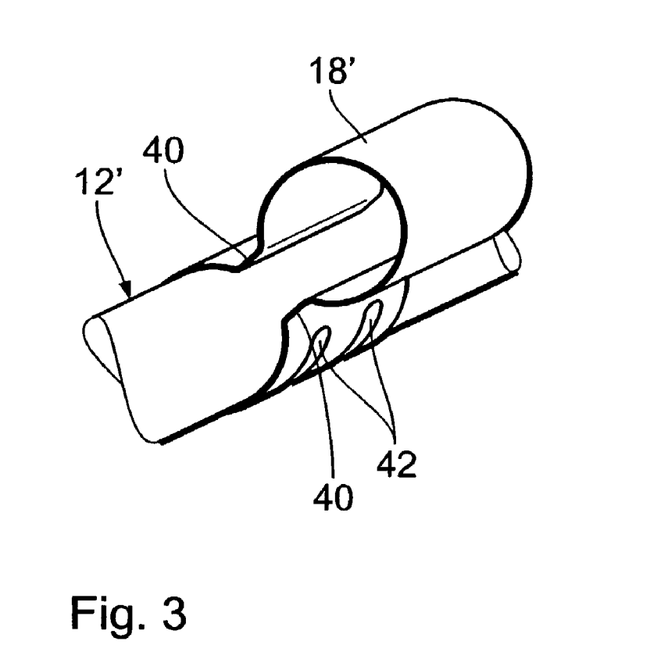
FIG. 3 shows a portion of a first electrode line with a longitudinal guide in the form of a Nitinol casing.

FIG. 3 shows a short portion of an atrial electrode line 12' with an alternative longitudinal guide 18' which is fitted in the form of a metal sleeve externally on the electrode line 12'. The configuration of the metal sleeve 18' with constrictions 40 is so selected that a ventricular electrode line introduced into the metal sleeve 18' assumes a lateral spacing relative to the atrial electrode line 12'. Constrictions 42 produced by crimping on the metal sleeve 18' provide for a secure hold on the atrial electrode line 12'.

Figure 4:
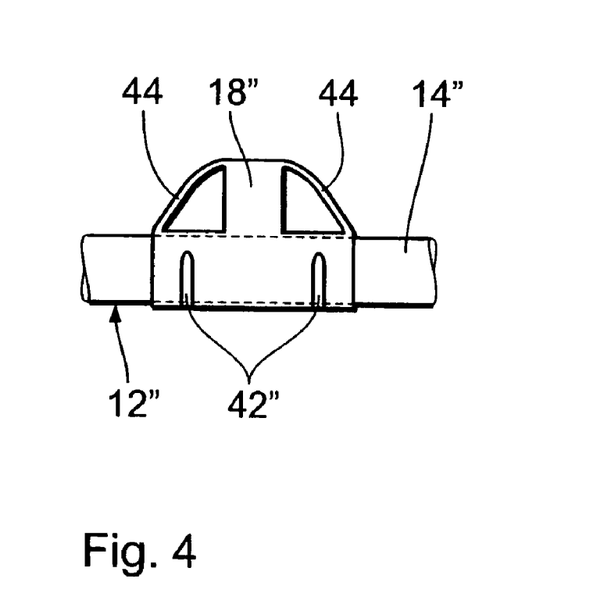
FIG. 4 shows a side view of a portion of a first electrode line with a longitudinal guide which has slopes.

FIG. 4 again shows a short portion of an atrial electrode line 12" with a longitudinal guide 18" mounted thereon. The longitudinal guide 18" is of a similar configuration to the longitudinal guide 18' of FIG. 3 and like it has holding constrictions 42" which are produced for example by crimping. In addition however the longitudinal guide 18" also has two slopes 44 which are of a bar-like configuration in the manner of a stent and which are intended to prevent the longitudinal guides 18" hooking into the tissue upon insertion of the atrial electrode line 12".

FIG. 5 again shows a short portion of an atrial electrode line 12''' with a longitudinal guide 18''' arranged thereon. The longitudinal guide 18''' is also preferably formed from metal such as for example Nitinol and has two loops 50 for holding purposes and for being guided along a ventricular electrode line. In addition the longitudinal guide 18''' has two tongues 52 which are shaped around the atrial electrode line 12''' and which overlap in the peripheral direction of the atrial electrode line 12'''. The tongues 52 perform on the one hand the function of providing the longitudinal guide 18''' with a hold on the atrial electrode line 12''', insofar as they implement a suitable clamping clip effect. In addition the thickness of the tongues 52 provides that a ventricular electrode line disposed in the longitudinal guide 18''' is at a spacing from the atrial electrode line 12'''. Therefore, constrictions such as the constrictions 40 of the longitudinal guide 18' in FIG. 3 can be omitted in the longitudinal guide 18'''.

Figure 5:
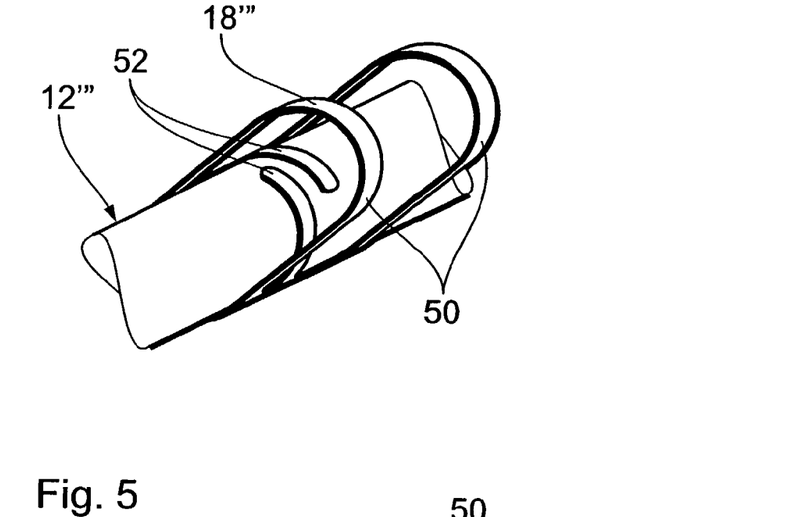
FIG. 5 shows a portion of an electrode line with a variant of a longitudinal guide which has spacing-producing tongues.
Figure 6:
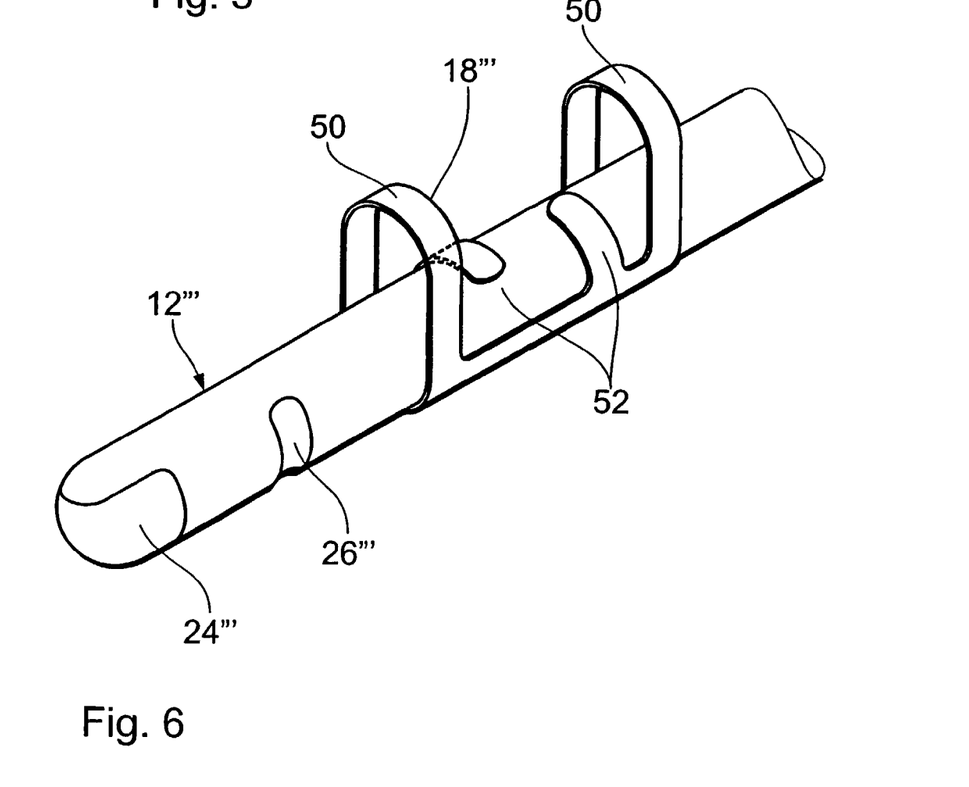
FIG. 6 shows the distal end of a first electrode line with partially insulated stimulation or sensing electrodes.

FIG. 6 shows the distal end of an atrial electrode line 12''' with a longitudinal guide 18''' as has already been described with reference to FIG. 5. It will be seen from FIG. 6 that the tip electrode 24''' and the ring electrode 26''' are insulated on that peripheral side of the atrial electrode catheter 12''', which in the implantation procedure is facing towards a ventricular electrode line and is moved past same. That peripheral direction is determined by the orientation of the longitudinal guide 18'''. The orientation of the longitudinal guide 18''' with respect to the atrial electrode line 12''' with the partially insulated electrodes 24''' and 26''' thereof is therefore to be so selected that the loops 50 of the longitudinal guide 18''' face in that peripheral direction in which the electrodes 24''' and 26''' of the atrial electrode line 12''' are insulated.

In accordance with the variant shown in FIG. 7, in comparison with the structure shown in FIG. 1, there is additionally a cable pull 60 which extends within the ventricular electrode line and issues at the distal end thereof. That cable pull is connected to the distal end of the atrial electrode line so that it is possible for the distal end of the atrial electrode line to be pulled by means of the cable pull in the direction of the distal end of the ventricular electrode line 14. For that purpose the cable pull extends within the ventricular electrode line to the proximal end thereof in order to be actuated from there.

In a variant which is not illustrated of an atrial electrode line with longitudinal guide or eye, the eye can be tipped with respect to the longitudinal axis of the atrial electrode line for example by means of a cable pull in such a way as to cause the eye to be clamped to a ventricular electrode line disposed in the eye so that the two electrode lines are fixed relative to each other.

As an alternative thereto the eye on the atrial electrode line can also be adapted to be deformed in some other manner in order to permit clamping to an electrode line in the eye.

It is also possible for the atrial electrode line to be deformed in the region of the eye, for example being bent in an S-shape or in some other manner, in such a way that the longitudinal axes of the atrial electrode line and the ventricular electrode line tend in the region of the eye not to extend parallel to each other, thus giving rise to bracing effects between the eye and the second electrode line disposed therein. During the insertion of the first atrial electrode line the deformation thereof is then removed for example by means of a suitable bar so that the atrial and ventricular electrode lines are easily longitudinally slidable relative to each other. Then—when the atrial electrode line has assumed the intended position—the bar is removed, the atrial electrode line, by virtue of its deformation, tilts the eye into engagement with the ventricular electrode line and the two electrode lines are fixed relative to each other.

What is claimed is:

1. An electrode arrangement for placement in a blood vessel, comprising:
    a first and a second electrode line, each having at least one stimulation and/or sensing electrode in a region of a distal end thereof;
    wherein a plurality of longitudinal guides for longitudinally receiving the second electrode line are disposed on said first electrode line along a length of the first electrode line such that said first electrode line cannot move longitudinally with respect to said longitudinal guides, and
    wherein each said longitudinal guide can be firstly adapted to permit relative longitudinal movement of the first electrode line with respect to the second electrode line, and
    wherein each said longitudinal guide can be secondly adapted to fix said first electrode line with respect to said second electrode line.

2. The electrode arrangement of claim 1, wherein:
    each said longitudinal guide comprises at least one eye having an inside diameter substantially corresponding to an outside diameter of the second electrode line.

3. The electrode arrangement of claim 1, wherein:
    the first and second electrode lines each have an outside diameter that is less than 2 mm.

4. The electrode arrangement of claim 1, wherein:
    the first electrode line is an electrode catheter for insertion into an atrium of a heart, and
    the second electrode line is an electrode catheter for insertion in a ventricle of the heart.

5. The electrode arrangement of claim 1 wherein each said longitudinal guide is secondly adapted by effecting a deformation of said longitudinal guides by temporarily applying a deformation means, and wherein said effected deformation is maintained after said deformation means is no longer applied.

6. The electrode arrangement of claim 1 wherein each said longitudinal guide is secondly adapted by a tipping of said longitudinal guides with respect to a longitudinal axis of said first electrode line.

7. The electrode arrangement of claim 1 wherein each said longitudinal guide is firstly adapted by temporarily removing an inherent deformation from said first electrode line in a region of said longitudinal guides.

8. The electrode arrangement of claim 7 wherein each said longitudinal guide is secondly adapted by having said inherent deformation of said first electrode line in a region of said longitudinal guides.

9. A first electrode line for use in placement in a blood vessel with a second electrode line in an electrode line arrangement, wherein the first electrode line comprises:
    a casing; and
    a plurality of longitudinal guides disposed thereon for longitudinally receiving to second electrode line such that said first electrode line cannot move longitudinally wit respect to said longitudinal guides, and
    wherein each said longitudinal guide can be firstly adapted to permit relative longitudinal movement of the first electrode line with respect to the second electrode line, and
    wherein each said longitudinal guide can be secondly adapted to fix said first electrode line with respect to said second electrode line.

10. The first electrode line of claim 9, wherein:
    each said longitudinal guide comprises at least one eye to slidably receive the second electrode line longitudinally.

11. The first electrode line of claim 10, wherein:
    at least one said longitudinal guide comprises a shape memory metal alloy.

12. The first electrode line of claim 11, wherein:
    the shape memory metal alloy is nitinol.

13. The first electrode line of claim 9, wherein:
    at least one said longitudinal guide comprises a shape memory metal alloy.

14. The first electrode line of claim 13, wherein:
    the shape memory metal alloy is nitinol.

15. The first electrode line of claim 12, wherein:
    at lout one said longitudinal guide has at least one sloped end in the longitudinal direction thereof, for preventing the longitudinal guide from hooking onto tissue as the first electrode line is inserted into the blood vessel.

16. The first electrode line of claim 14, wherein:
    at least one said longitudinal guide has at least one sloped end in to longitudinal direction thereof, for preventing to longitudinal guide from hooking onto tissue as to first electrode line is inserted into to blood vessel.

17. The first electrode line of claim 9, wherein:
    at least one said longitudinal guide has at least one sloped end in the longitudinal direction thereof, for preventing the longitudinal guide from hooking onto tissue as to first electrode line is inserted into the blood vessel.

18. The first electrode line of claim 10, wherein:
each said longitudinal guide is mountably affixed to said casing of the first electrode line.

19. The first electrode line of claim 17, wherein:
each said longitudinal guide is mountably affixed to said casing of the first electrode line.

20. The first electrode line of claim 9, wherein:
each said longitudinal guide is mountably affixed to said casing of the first electrode line.

21. The first electrode line of claim 18, wherein:
at least one said longitudinal guide comprises at least one friction-reducing tongue, arranged between the casing of the first electrode line and a hollow portion of the longitudinal guide for receiving the second electrode line, such that said at least one tongue spaces the electrode line casing apart from the second electrode line.

22. The first electrode line of claim 19, wherein:
at least one said longitudinal guide comprises at least one friction-reducing tongue, arranged between the easing of the first electrode line and a hollow portion of the longitudinal guide for receiving the second electrode line, such that said at least one tongue spaces the electrode line casing apart from the second electrode line.

23. The first electrode line of claim 20, wherein:
at least one said longitudinal guide comprises at least one friction-reducing tongue, arranged between the casing of the first electrode line and a hollow portion of the longitudinal guide for receiving the second electrode line, such that said at least one tongue spaces the electrode line casing apart from the second electrode line.

24. The first electrode line of claim 10, herein:
each said longitudinal guide is formed as an integral part of said casing of the first electrode line.

25. The first electrode line of claim 17, wherein:
each said longitudinal guide is formed as an integral part of said casing of the first electrode line.

26. The first electrode line of claim 9, wherein:
each said longitudinal guide is formed as an integral part of said casing of the first electrode line.

27. The first electrode line of claim 24, further comprising:
a tip electrode, operatively connected at a distal end of said first electrode line, having a peripheral portion thereof insulated, the insulated portion facing in the peripheral direction as to longitudinal guides face.

28. The first electrode line of claim 25, further comprising:
a tip electrode, operatively connected at a distal end of said first electrode line, having a peripheral portion thereof insulated, the insulated portion facing in to same peripheral direction as the longitudinal guides face.

29. The first electrode line of claim 26, further comprising:
a tip electrode, operatively connected at a distal end of said first electrode line, having a peripheral portion thereof insulated, the insulated portion facing in the peripheral direction as the longitudinal guides face.

30. The first electrode line of claim 9, wherein:
at least one said longitudinal guide is pivotable or tiltable relative to a longitudinal axis of the first electrode line such that, in the pivoted or tilted condition, the longitudinal guide is adapted to be clamped to the second electrode line disposed therein.

31. The first electrode line of claim 9, wherein:
the first electrode line is bent in a region of at least one said longitudinal guides, in the direction of the longitudinal axis.

32. The first electrode line of claim 31, wherein:
the first electrode line is bent in an S-shape.

33. The first electrode line of claim 31, wherein:
the first electrode line is pre-bent.

* * * * *

UNITED STATES PATENT AND TRADEMARK OFFICE
CERTIFICATE OF CORRECTION

| | | Page 1 of 1 |
|---|---|---|
| PATENT NO. | : 7,561,924 B2 | |
| APPLICATION NO. | : 10/278040 | |
| DATED | : July 14, 2009 | |
| INVENTOR(S) | : Kolberg et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1295 days.

Signed and Sealed this

Fourth Day of January, 2011

David J. Kappos
*Director of the United States Patent and Trademark Office*